United States Patent [19]

Müller et al.

[11] Patent Number: 6,036,962
[45] Date of Patent: *Mar. 14, 2000

[54] COSMETIC COMPOSITIONS COMPRISING SULFONATE GROUPS CONTAINING POLYAMIDES

[75] Inventors: Wolfgang Müller, Frankenthal; Stefan Stein, Saulheim; Jörg Breitenbach, Mannheim; Axel Sanner, Frankenthal; Karin Sperling, Neustadt, all of Germany

[73] Assignee: BASF Aktiengesellschaft, Ludwigshafen, Germany

[ * ] Notice: This patent is subject to a terminal disclaimer.

[21] Appl. No.: 08/790,734

[22] Filed: Jan. 27, 1997

[30] Foreign Application Priority Data

Feb. 12, 1996 [DE] Germany ............... 196 05 076

[51] Int. Cl.$^7$ ...................................... A61K 7/48
[52] U.S. Cl. ............ 424/401; 424/61; 424/70.1; 424/70.17
[58] Field of Search ................ 424/401, 61, 70.1, 424/70.17

[56] References Cited

U.S. PATENT DOCUMENTS 5,846,524  12/1998  Breitenbach et al. ............... 424/70.17

OTHER PUBLICATIONS

Fisch et al., Chemical Abstracts, vol. 124, #241746, 1995.

Primary Examiner—Jyothsna Venkat
Attorney, Agent, or Firm—Keil & Weinkauf

[57] ABSTRACT

The present invention relates to the use of polyamides in cosmetics which carry sulfonate groups and are obtainable from $A_1$) from 0 to 19.9 mol-% of at least one monoaminocarboxylic acid having 2 to 12 carbon atoms, its lactam, or monoaminocarboxylic acid/lactam mixtures, $A_2$) from 40.05 to 50 mol-% of at least one diamine having 2 to 18 carbon atoms, $A_3$) from 0.5 to 49.5 mol-% of at least one dicarboxylic acid having 4 to 12 carbon atoms which carries sulfonate groups, and $A_4$) from 0.5 to 49.5 mol-% of at least one further dicarboxylic acid having 2 to 16 carbon atoms, and cosmetic compositions containing said polyamides.

8 Claims, No Drawings

COSMETIC COMPOSITIONS COMPRISING SULFONATE GROUPS CONTAINING POLYAMIDES

The present invention relates to the use of polyamides which carry sulfonate groups for treating keratin-containing structures, and to cosmetic compositions containing these polyamides.

For the setting, structural improvement and shaping of keratin-containing structures, synthetic polymers are generally used. Established polymers are, for example, those based on vinylpyrrolidone and vinyl acetate, which are commonly applied in the form of alcoholic or aqueous-alcoholic solutions.

The solutions of these materials form a film on the surface of the treated keratin-containing structures. The film, depending on the type of polymer employed, may have a setting, structure-improving, shaping, shine-enhancing, smoothing and antistatic action. The films formed on the keratin-containing structures are intended, on the one hand, to be resistant to moisture, but on the other hand these films should be able to be removed easily in the course of cleaning using an aqueous surfactant solution.

Because of the continually increasing demand for more eco-compatible products, the content of volatile organic constituents or compounds (VOC) is to be kept as low as possible and/or reduced in cosmetic preparations as well, for example hairsprays, hair gels, foam setting lotions or nail varnish. This means that alcohol is to be increasingly replaced by water as solvent.

When conventional film-forming polymers are used, however, this may present difficulties, since at relatively high water contents the application properties of the compositions for treating keratin-containing structures, and the drying of the polymer films, are unsatisfactory. Brittleness and reduced transparency of the resulting films are possible unwanted consequences.

U.S. Pat. No. 3,296,204 discloses the preparation of sulfonate-containing polyamides by condensation of sulfonated aromatic dicarboxylic acids, the sulfonic acid groups of which are present as alkali metal salt, with diamines. The polyamides are employed in textile industry.

DE-C 23 08 266 describes the use of sulfonated polyamides for producing polyamide yarns.

FR 2 685 001 discloses the use of certain water-dispersible polyamides for the finishing of textile fibers.

U.S. Pat No. 4,300,580 describes the use of water-dispersible polyesters which carry sulfonate groups as hair grooming compositions. However, they suffer from the disadvantage of being hardly removable from hair by washing.

U.S. Pat. No. 5,158,762 relates to aqueous hairspray compositions in which the film formers used are polymer blends of a water-soluble polymer and a polyesteramide or polyester containing sulfonate groups.

It is the object of the present invention to find polymers which are suitable for use as film formers in compositions for treating keratin-containing structures and which permit increased proportions of water in the corresponding cosmetic preparations without any adverse effect on performance characteristics, such as the application properties. Furthermore, the films present after application should be non-tacky, clear, smooth and elastic with a good structure-improving action. They should be on the one hand highly durable but on the other hand also easy to remove.

Surprisingly, we have found that this object is achieved by polyamides which carry sulfonate groups and which are obtainable from $A_1$) from 0 to 19.9 mol-%, preferably from 0 to 10 mol-%, particularly preferably from 0 to 5 mol-%, of at least one monoaminocarboxylic acid having 2 to 12 carbon atoms, its lactam, or monoaminocarboxylic acid/lactam mixtures, $A_2$) from 40.05 to 50 mol-%, preferably from 45 to 50 mol-%, particularly preferably from 47.5 to 50 mol-%, of at least one diamine having 2 to 18 carbon atoms, $A_3$) from 0.5 to 49.5 mol-%, preferably from 5 to 35 mol-%, particularly preferably from 10 to 30 mol-%, of at least one dicarboxylic acid having 4 to 12 carbon atoms which carries sulfonate groups, and $A_4$) from 0.5 to 49.5 mol-%, preferably from 15 to 45 mol-%, particularly preferably from 20 to 40 mol-%, of at least one further dicarboxylic acid having 2 to 16 carbon atoms, the sum of the molar proportions of monomers $A_3$) and $A_4$) preferably corresponding to the molar proportion of the monomer $A_2$).

Thus, the present invention relates to cosmetic compositions, in particular aqueous compositions, which contain the polyamides described above. Preferably the present invention relates to compositions for treating keratin-containing structures, in particular hair, nails or skin.

The present invention relates further to the use of the polyamides according to the present invention in the field of cosmetics, preferably for treating keratin-containing structures, in particular hair, nails or skin.

The invention further relates to a cosmetic process, preferably for treating keratin-containing structures, in particular hair, nails or skin, wherein the polyamides according to the present invention are applied such that the desired effect is obtained. This is generally achieved by application of an effective amount of the polyamides to the keratin-containing structures.

Particularly suitable polyamides are those obtainable only from monomers $A_2$), $A_3$) and $A_4$), the molar proportion of the monomer $A_2$ preferably being 50 mol-% and, consequently, the sum of the molar proportions of monomers $A_3$) and $A_4$) likewise being 50 mol-%.

It is particularly advantageous if at least two different diamines are used to prepare the present polymers.

Suitable monomers $A_1$) are the monoaminocarboxylic acids which are known for the preparation of polyamides, or lactams thereof, for example ωaminoundecanoic acid, ε-caprolactam, laurolactam, caprylolactam or enantholactam.

Possible monomers $A_2$) are substituted or unsubstituted aliphatic, cycloaliphatic or aromatic diamines. Examples of suitable diamines are alkylenediamines or cycloalkyldiamines, such as 1,5-pentanediamine, 4,4'-diaminodicyclohexylmethane, 2,2'-(4,4'-diaminodicyclohexyl)propane, 3,3'-dimethyl-4,4'-diaminodicyclohexylmethane or, preferably, hexamethylenediamine. Also suitable are piperazine, 2,2,4-trimethylhexamethylenediamine, 2-butyl-2-ethyl-1,5-pentanediamine, 2-methylpentamethylenediamine, isophorone diamine or 4,7-dioxadecane-1,10-diamine.

The branched diamines are particularly advantageous, since they favorably affect the properties of the formed films by, for example, reducing the crystallinity.

Possible monomers $A_3$) which carry sulfonate groups are those in which the sulfonate group is present in salt form, for example as the salt of an alkali metal, such as lithium, sodium or potassium, or an ammonium group which is unsubstituted or substituted by one to four aliphatic or aromatic groups. Suitable monomers carrying sulfonate groups are salts of aliphatic or aromatic dicarboxylic acids, for example sulfosuccinic acid or 5-sulfopropoxyisophthalic acid. Preference is given to using the sodium salt of 5-sulfoisophthalic acid.

Examples of suitable monomers $A_4$) are aliphatic dicarboxylic acids, such as sebacic acid, azelaic acid, dodecanedicarboxylic acid or, preferably, adipic acid or sebacic acid. Examples of suitable aromatic dicarboxylic acids are isophthalic acid or terephthalic acid, which can also be substituted, examples being 3-tert-butylisophthalic acid, and also 3,3'- or 4,4'-diphenyldicarboxylic acid, 3,3'- or 4,4'-diphenylmethanedicarboxylic acid, 3,3'- or 4,4'-diphenyl sulfone-dicarboxylic acid, 1,4- or 2,6-naphthalenedicarboxylic acid or 2-phenoxyterephthalic acid.

It is of course true for all monomer groups that mixtures of the respective monomers can also be employed.

The polyamides which carry sulfonate groups can be prepared in a manner known per se.

A preferred preparation procedure which may be mentioned is the batch procedure (discontinuous procedure). In this case the aqueous monomer solution is heated in an autoclave to from 240 to 300° C. over a period of from 0.5 to 3 h, during which a pressure of from 10 to 50 bar, in particular from 15 to 30 bar, is reached which is held constant for up to 4 h by releasing excess steam. The autoclave is then let down to atmospheric pressure at constant temperature over a period of from 0.5 to 3 h. The polymer melt is then removed from the autoclave, cooled with air or nitrogen and subsequently granulated.

The resulting copolyamide generally has a viscosity number of from 25 to 110 ml/g, preferably from 30 to 80 ml/g, measured on a 0.5% strength by weight solution in 96% strength sulfuric acid.

To prepare the polyamide dispersions or solutions according to the present invention, the polyamide granules can be dispersed or dissolved in water by intense stirring in a proportion of from 30 to 99% by weight, preferably from 60 to 90% by weight, based on the quantity of polymer. The dispersions or solutions are customarily prepared at 25° C. but can also be prepared at up to 80° C. After adding water, the mixtures are preferably stirred for from 0.5 to 3 h more, a period during which complete dispersion or dissolution of the polyamides takes place. The resulting dispersions or solutions have solids contents of from 1 to 70% by weight, preferably from 10 to 40% by weight. The transparency (determined using a Vis spectrometer from Beckmann) is from 50 to 99%, preferably>60%. The particle sizes can be in the range from 40 to 120 nm.

An advantage of the polyamides according to the present invention, which carry sulfonate groups, is that they can be processed without problems in water to give dispersions or solutions having relatively high solids contents.

The polyamides according to the present invention are therefore particularly suitable for those compositions, destined for the treatment of keratin-containing structures, that are intended to have a particularly low VOC content, ie. are based predominantly on water. They can be employed with preference in hairsetting compositions having VOC levels<55% by weight. Owing to the good autodispersibility of the polyamides according to the present invention it is possible to dispense with significant proportions of organic solvents.

However, also suitable in accordance with the invention as film formers in compositions for treating keratin-containing structures are those polyamides, containing sulfonate groups, which are obtainable by using lesser or greater proportions of the monomers which carry sulfonate groups, especially when the compositions for treating keratin-containing structures can have VOC levels of>55%. In this case the compositions for treating keratin-containing structures constitute alcoholic or aqueous-alcoholic solutions of the polyamides in other organic solvents suitable for the purpose. Owing to the better evaporation properties of the organic solvent in comparison with water, these solutions can also be employed with a relatively low solids content, for example in the range from 1 to 10% by weight, as compositions for treating keratin-containing structures.

In accordance with the invention the sulfoiate-carrying polyamides can be employed both as sole film formers in compositions for treating keratin-containing structures and as mixtures with customary film-forming polymers. Examples of suitable customary film-forming polymers are anionic polymers, such as acrylic acid or methacrylic acid homopolymers or copolymers, copolymers of acrylic acid and acrylamides, and copolymers based on alkyl vinyl ethers and maleic acid monoalkyl esters, amphoteric polymers, such as copolymers of octylacrylamide, acrylate and butylaminoethyl methacrylate, and also nonionic polymers, such as vinylpyrrolidone homopolymers, vinylpyrrolidone-vinyl acetate copolymers, and copolymers of vinylpyrrolidone, vinyl acetate and vinyl propionate. The ratio of polyamides containing sulfonate groups to the customary film-forming polymers can be chosen in accordance with the performance characteristics desired.

Furthermore, the compositions for treating keratin-containing structures can also contain customary auxiliaries, examples being surfactants, emulsifiers and fragrances.

Examples of possible formulations for treating keratin-containing structures are composed of (%=% by weight):

| | | |
|---|---|---|
| 1) | 5% | of a polyamide |
| | 0.2% | of a mixture of perfume oil and emulsifier in a ratio of 1:3 |
| | 10% | of ethanol |
| | 84.8% | of water |
| 2) | 3.5% | of a polyamide |
| | 1.5% | of a copolymer of 60% by weight N-vinylpyrrolidone and 40% by weight vinyl acetate |
| | 0.2% | of perfume oil/emulsifier |
| | 94.8% | of water |

Instead of an NVP/VA copolymer it is also possible, for example, to use 1.5% of an acrylate-based terpolymer.

When the compositions for treating keratin-containing structures according to the present invention are employed, clear, well-drying films are obtained which give a pleasant feeling to the skin, exert a good setting effect and can be removed with ease.

EXAMPLES 1 to 6
(Table 1)

2 kg of a monomer mixture having the composition shown in Table 1 were charged in 1500 ml of water to a 5 l laboratory autoclave. The autoclave was heated to 280° C. over the course of 1 h, the resulting pressure of about 20 bar being kept constant by releasing excess steam. The temperature and pressure remained unaltered for a further hour. The autoclave was then let down to atmospheric pressure over the course of 1 hour while maintaining the temperature at 280° C. Post-condensation was then carried out for 2 h in a stream of nitrogen. The melt was subsequently discharged via a die, cooled in an airbed and granulated.

400 g portions of the granules were dispersed with stirring in 600 g of water at room temperature.

The following tests were carried out on the granules:

a) granules prior to dispersion: determination of the viscosity number (VN) in accordance with DIN 53 246 (0.5% strength solution of the copolyamide in 95% strength $H_2SO_4$)

b) Determination of the glass transition temperature (Tg) and of the melting range by means of differential scanning calorimetry (DSC 5000 from Mettler) at a heating rate of 20° C./min.

The dispersions were characterized in accordance with the following methods:

a) determination of the turbidity (NTU value)

The turbidity was determined by means of nephelometric analysis (modified method in accordance with DIN 38404). This method involves the photometric determination of light scattering after transmission of the test solution, the scattering depending on the interaction between the light beam and the particles in the solution or dispersion. The number and the size of said particles constitute the degree of turbidity. The measureable variable is the nephelometric turbidity unit (NTU value) determined in 5% strength aqueous solution at 25° C. and calibrated on the basis of formazine as artificial turbidity agent. The higher the NTU value, the more turbid the solution.

b) determination of the viscosity in a rotary viscometer (model: RV 20; Haake) at a shear of 500 $s^{-1}$; T=23° C.

TABLE 1

Composition and properties in accordance with Examples 1 to 6 (data in mol-%)

|  | Example 1 | Example 2 | Example 3 | Example 4 | Example 5 | Example 6 |
|---|---|---|---|---|---|---|
| 5-Sulfoisophthalic acid sodium salt | 15.2 | 20 | 20 | 20 | 20 | 20 |
| Isophthalic acid | 24.8 | 20 | 20 | 20 | 20 | 10 |
| Hexamethylenediamine | 36 | 20 | 30 | 20 | 25 | 20 |
| AH salt | 20 | 20 | 20 | 15 | 20 | 20 |
| II-Aminoundecanoic acid | — | — | — | 5 | 10 | — |
| 2-Methylpentamethylene diamine | — | 20 | 5 | 20 | 5 | — |
| Isophorone diamine | 4 | — | — | — | — | 10 |
| 2,2,4-Trimethylhexamethylene diamine | — | — | 5 | — | — | 10 |
| Itaconic acid | — | — | — | — | — | 10 |
| VN [ml/g] | 47 | 40 | 38 | 43 | 20 | 32 |
| dyn. visc. [mPas] (5% in $H_2O$) | 2,82 | 3,16 | 2,72 | 2,82 | 3,13 | 3,33 |
| glass transition temperature $T_g$ [° C.] | 152 | 154 | 156 | 157 | 117 | 147 |
| NTU value (5% in $H_2O$) | 3,7 | 1,8 | 6,4 | 7,8 | 6,8 | 10,4 |

We claim:

1. A cosmetic composition comprising a polyamide which carries sulfonate groups and is obtainable from $A_1$) from 0 to 19.9 mol-% of at least one monoaminocarboxylic acid having 2 to 12 carbon atoms, its lactam, or monoaminocarboxylic acid/lactam mixtures, $A_2$) from 40.05 to 50 mol-% of at least one diamine having 2 to 18 carbon atoms, $A_3$) from 0.5 to 49.5 mol-% of at least one dicarboxylic acid having 4 to 12 carbon atoms which carries sulfonate groups, and $A_4$) from 0.5 to 49.5 mol-% of at least one further dicarboxylic acid having 2 to 16 carbon atoms.

2. A composition as claimed in claim 1, wherein the polyamide is obtainable from $A_1$) from 0 to 10 mol-% of at least one monoaminocarboxylic acid having 2 to 12 carbon atoms, its lactam, or monoaminocarboxylic acid/lactam mixtures, $A_2$) from 45 to 50 mol-% of at least one diamine having 2 to 18 carbon atoms, $A_3$) from 5 to 35 mol-% of at least one dicarboxylic acid having 4 to 12 carbon atoms which carries sulfonate groups, and $A_4$) from 15 to 45 mol-% of at least one further dicarboxylic acid having 2 to 16 carbon atoms.

3. A cosmetic composition comprising a polyamide which carries sulfonate groups and is obtainable from $A_2$) at least one diamine having 2 to 18 carbon atoms, $A_3$) at least one dicarboxylic acid having 4 to 12 carbon atoms which carries sulfonate groups, and if desired $A_4$) at least one further dicarboxylic acid having 2 to 16 carbon atoms.

4. A composition as claimed in claim 3, wherein the polyamide is obtainable from $A_2$) 50 mol-% of at least one diamine having 2 to 18 carbon atoms, $A_3$) from 0.5 to 49.5 mol-% of at least one dicarboxylic acid having 4 to 12 carbon atoms which carries sulfonate groups, and $A_4$) from 0.5 to 49.5 mol-% of at least one further dicarboxylic acid having 2 to 16 carbon atoms.

5. A composition as claimed in claim 1, wherein the polyamide which carries sulfonate groups is obtainable from at least two different diamines.

6. A composition as claimed in claim 1 for treating keratin-containing structures.

7. A composition as claimed in claim 6 for treating hair, nails or skin.

8. A composition as claimed in claim 6, additionally comprising further film-forming polymers.

* * * * *